United States Patent
Maschke

(10) Patent No.: US 7,704,210 B2
(45) Date of Patent: Apr. 27, 2010

(54) MEDICAL DEVICE FOR REMOVING A VASCULAR OCCLUSION

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 901 days.

(21) Appl. No.: 11/092,780

(22) Filed: Mar. 29, 2005

(65) Prior Publication Data

US 2005/0234343 A1 Oct. 20, 2005

(30) Foreign Application Priority Data

Mar. 31, 2004 (DE) .................. 10 2004 015 641

(51) Int. Cl.
*A61B 8/12* (2006.01)
*A61B 17/22* (2006.01)
(52) U.S. Cl. .................. 600/471; 606/205; 606/159; 600/467
(58) Field of Classification Search .................. 600/424, 600/471, 467, 439; 606/159, 205, 198
See application file for complete search history.

(56) References Cited

U.S. PATENT DOCUMENTS

| 5,741,270 | A |  | 4/1998 | Hansen et al. |
| 5,908,437 | A | * | 6/1999 | Asano et al. .................. 606/205 |
| 6,120,516 | A | * | 9/2000 | Selmon et al. .............. 606/159 |
| 6,266,550 | B1 | * | 7/2001 | Selmon et al. .............. 600/407 |
| 6,746,462 | B1 | * | 6/2004 | Selmon et al. .............. 606/159 |
| 6,800,085 | B2 | * | 10/2004 | Selmon et al. .............. 606/198 |
| 2002/0019644 | A1 | * | 2/2002 | Hastings et al. ............. 606/159 |
| 2002/0029052 | A1 | * | 3/2002 | Evans et al. .................. 606/159 |
| 2003/0236443 | A1 | * | 12/2003 | Cespedes et al. .............. 600/29 |
| 2004/0006370 | A1 |  | 1/2004 | Tsugita |
| 2007/0066888 | A1 | * | 3/2007 | Maschke ..................... 600/424 |

* cited by examiner

*Primary Examiner*—Eric F Winakur
*Assistant Examiner*—Helene Bor

(57) ABSTRACT

Device for removing a complete vascular occlusion using a CTO catheter, at the distal end of which are disposed stretching tongs and IVUS monitoring, whereby the CTO catheter is combined with an IVUS catheter to form an integrated unit.

9 Claims, 2 Drawing Sheets

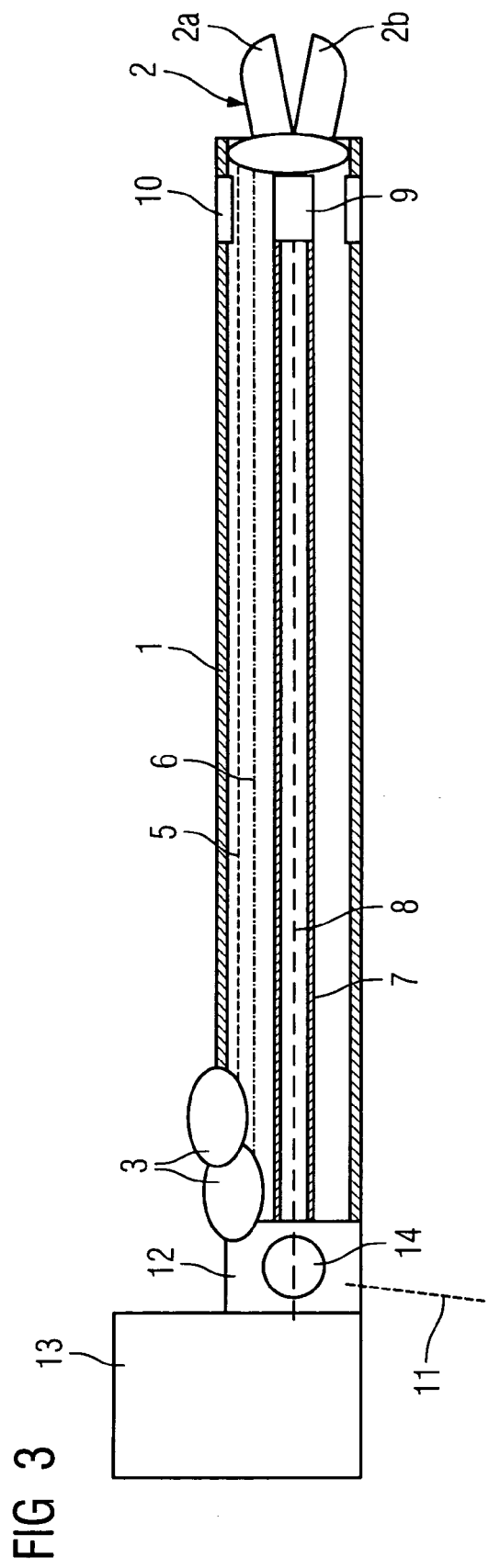
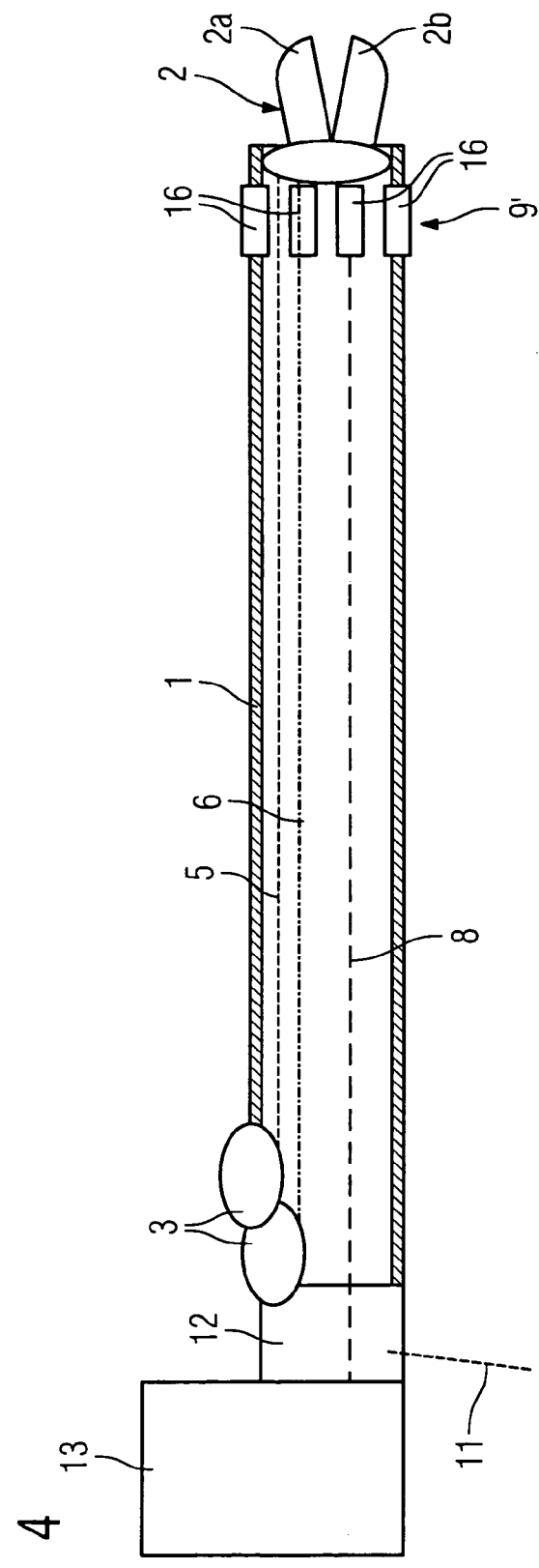

MEDICAL DEVICE FOR REMOVING A VASCULAR OCCLUSION

CROSS REFERENCE TO RELATED APPLICATIONS

This application claims priority to the German application No. 10 2004 015 641.7, filed Mar. 31, 2004 which is incorporated by reference herein in its entirety.

FIELD OF INVENTION

The invention relates to a device for removing a complete vascular occlusion using a CTO catheter with stretching tongs and IVUS monitoring disposed at the distal end.

BACKGROUND OF INVENTION

Vascular disease, in particular cardiac infarction, is one of the most common fatal illnesses. It is caused by disease of the coronary arteries (arterios clerosis), in which the build-up of deposits (arteriosclerotic plaque) causes occlusions in the coronary arteries. In particularly serious cases this can result in a complete occlusion of the coronary vessels, which is known as a "Chronic Total Coronary Occlusion" (CTO). These occlusions have in the past generally been treated only by means of a bypass operation. In recent years laser angioplasty (PTLA) has additionally become established as a way of removing plaque, particularly in the case of long stenoses (>2 cm) and in the case of complete occlusions. However, PTLA involves a considerable risk of injury in the form of hemorrhage, damage or perforation/dissection of the vascular wall.

In February 2002 the FDA authorized a new instrument—known as a CTO catheter—to remove the CTO. This device works in a similar way to stretching tongs and presses out the plaque in the coronary arteries piece by piece and permits a gradual removal of the entire vascular occlusion. Such a CTO catheter to remove the CTO is described, for example, in U.S. Pat. No. 5,741,270 "Manual Actuator for a Catheter System for Treating a Vascular Occlusion" and in U.S. Pat. No. 6,120, 516 "Method for Treating Vascular Occlusion", in particular FIG. 18. As a product, the Frontrunner CTO catheter from LuMend, Inc., Redwood City, Calif. is known.

SUMMARY OF INVENTION

The intervention with the CTO catheter is implemented using an angiography system under x-ray monitoring. The drawback of this method is that the coronary arteries are only shown in two dimensions and only the actual stenosis is shown on the x-ray image. In order to make the vessel clearly visible, it is additionally necessary to inject contrast medium into the coronary arteries. In some patients contrast medium allergies are known or patients report a sudden heat flush. In addition, during the intervention it is difficult for medical staff to distinguish between plaque and vessel wall. This increases the risk that the "stretching tongs" will be positioned in the wrong places and that damage will occur to the vessel wall.

The introduction of an IVUS (intravascular ultrasound) catheter into the vessel enhances the imaging information, yet has the disadvantage that a relatively expensive catheter must also be inserted into the patient and must be removed from the vessel before the CTO catheter is inserted. An IVUS system is described, for example, in EP 0 885 594 B1 and in U.S. Pat. No. 5,193,546.

An object of the invention is therefore to configure a device of the type specified above, to provide an optimum device which is easy to use and which enables the point of intervention to be directly monitored, even during the vessel dilatation if necessary, without the tedious process of changing the various catheters.

This object is achieved according to the invention in that the CTO catheter is combined with an IVUS catheter to form an integrated unit, whereby rotating IVUS signal lines are preferably disposed in the tubular catheter sheath of the CTO catheter alongside the mechanical activation lines for the stretching tongs, said rotating IVUS signal lines leading to an IVUS sensor which can be disposed within a circumferential ring-shaped window directly behind the stretching tongs, or—movably through an opening of the stretching tongs—directly forward of the stretching tongs. Rotating the IVUS signal line—unlike the necessary rotation of the IVUS sensor—is not essential, but is expedient.

The embodiment according to the invention provides an integrated module comprising a CTO catheter with an IVUS catheter integrated therein, representing an optimum system for opening up complete vascular stenoses. The great advantage of the solution lies in the reduction in process stages and in the catheters used, and also in the reduction of x-rays applied. The IVUS system images provide important additional medical information with high resolution, particularly at close range over the plaque and the vascular wall. This means that the plaque can be identified, and can be removed by using the CTO "stretching tongs" at the right locations, and the success of the procedure can then be checked immediately without subjecting the patient to unnecessarily high levels of contrast media or x-rays. Furthermore, the risk of damage to the vascular wall is reduced.

In a development of the invention, provision may be made for the IVUS signal line to be located inside a hollow, flexible drive shaft for the IVUS sensor.

In order to dispose the IVUS sensor forward of the stretching tongs, thereby enabling a direct observation of the complete stenosis be fore the start of treatment, the drive shaft for the IVUS sensor should be accommodated in the catheter sheath with the IVUS signal lines running therein so as to slide through the previously mentioned opening in the center of the stretching tongs. After the first observation of the complete stenosis, the IVUS sensor is withdrawn in the CTO catheter sheath, so that the stretching tongs can then be deployed. The sensor can then be moved forward again, in order to observe the result of the work and so forth, so that the complete vascular stenosis can gradually be gently opened.

Instead of the previously described arrangement with a rotating IVUS sensor, in a further embodiment of this invention provision can be made for IVUS signal lines to be disposed in the tubular flexible sheath of the CTO catheter alongside the mechanical activation lines for the stretching tongs, whereby said IVUS signal lines lead to a sensor array comprising a plurality of ultrasound transducers, said sensor array being integrated in the catheter sheath directly behind the stretching tongs. The provision of such a circumferential sensor array, in which the individual ultrasound transducers function simultaneously as transmitters and receivers, means that a rotating IVUS sensor is not required and, of course, no drive shaft either. In this way rotating couplings for connecting the corresponding components of the combined catheter to the stationary power supply unit are likewise no longer required.

This arrangement of a combined CTO-IVUS catheter is particularly suitable for an arrangement in which the IVUS sensor is to be disposed forward of the stretching tongs, since a rotating drive shaft for the IVUS sensor is not required here, but the staggered scanning of the vascular wall is instead achieved by the staggered time control of the ultrasound transducers of the sensor array.

According to a further feature of this invention, the CTO catheter sheath is to be provided with inlet and outlet openings at each end for a contrast medium.

In addition to magnets, which may be disposed in the vicinity of the CTO catheter tip for the purpose of magnetic navigation in the vessel, provision may also be made for an inflatable and preferably multi-chambered balloon, which is used for fixing the catheter in the vessel and/or for vascular dilatation, to be disposed on the CTO catheter tip.

Finally, there is also scope within the invention for the device to have a guidewire or guiding catheter running through it.

A typical procedure using a device according to the invention is described below.

A guidewire or guiding catheter is inserted under x-ray monitoring, using contrast media as required, until the target position (stenosis) is reached.

The integrated CTO-IVUS catheter is inserted under x-ray monitoring, using contrast media as required, until the target position is reached.

When the required target position is reached, the irrigation fluid is injected for the IVUS procedure and the point at which the plaque is to be removed is observed with high resolution.

The CTO intervention is then carried out gradually on the plaque, whereby it is possible for the progress to be inspected by means of IVUS after each dilatation.

Once the intervention has been completed, the entire vessel section is inspected once again by means of IVUS.

In addition to the combined CTO-IVUS catheter as described above, the device according to the invention comprises a device for connecting the proposed catheter to a user interface for the component of the integrated catheter that is used for plaque ablation. As well as a signal interface unit and a preprocessing stage for the IVUS image data, an image processing and image display unit including image memory is provided. A power supply unit and network interface are of course also available.

The IVUS imaging system can be expanded by the addition of menus to facilitate the quantification of the stenoses to be removed, for example the level of stenosis before and after the intervention. In addition, the user interface may incorporate input options for inputting patient data and data for the catheter parameter via keyboard and/or barcode or a mouse.

BRIEF DESCRIPTION OF THE DRAWINGS

Other advantages, features and details of the invention are explained in the following description of certain exemplary embodiments, on the basis of the diagrams in which:

FIG. 3 shows a schematic view of the structure of a combined CTO-IVUS catheter according to the invention with an IVUS sensor disposed directly behind the stretching tongs, and FIG. 4 shows a diagrammatic illustration of a modified exemplary embodiment of a combined CTO-IVUS catheter according to the invention, whereby instead of a rotating IVUS sensor a plurality of ultrasound transducers forming a sensor array are incorporated into the catheter sheath.

DETAILED DESCRIPTION OF INVENTION

Figure 1:
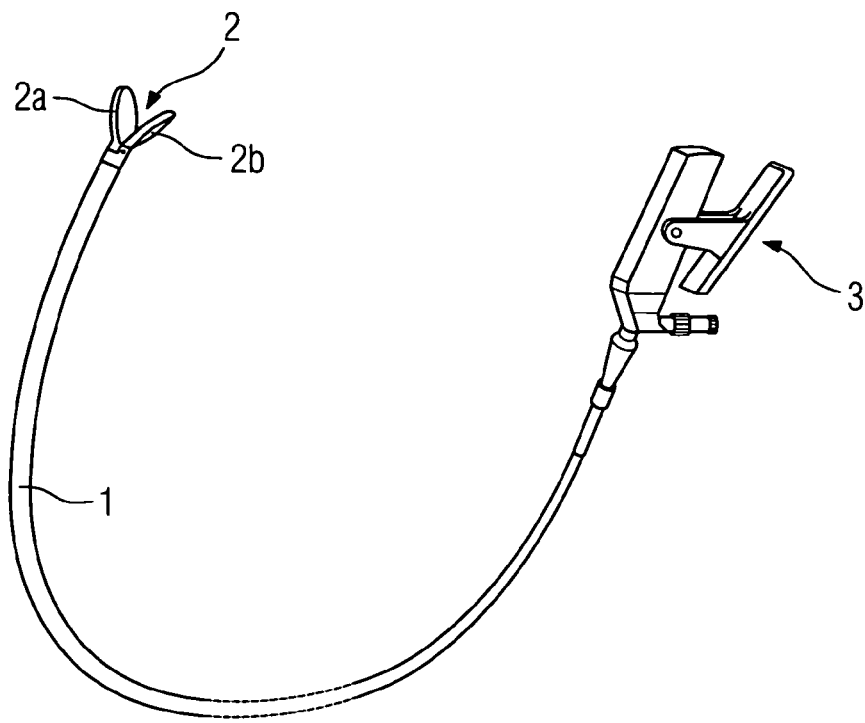
FIG. 1 shows an illustration of a CTO catheter.
Figure 2A:
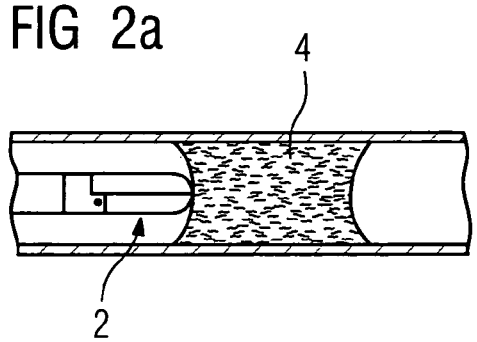
FIGS. 2a to 2d show diagrammatic illustrations of the removal of a complete stenosis using such a CTO catheter at different points in time of the intervention.
Figure 2B:
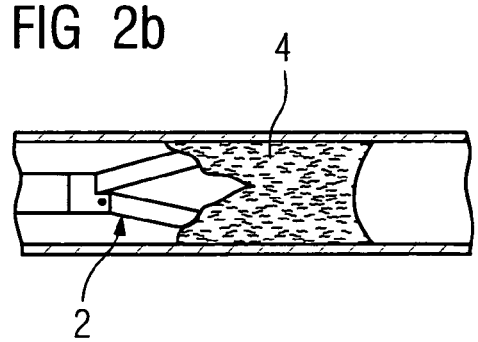
Figure 2C:
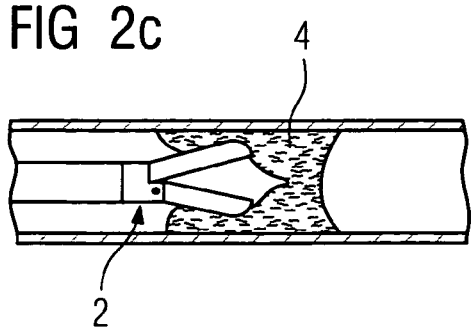
Figure 2D:
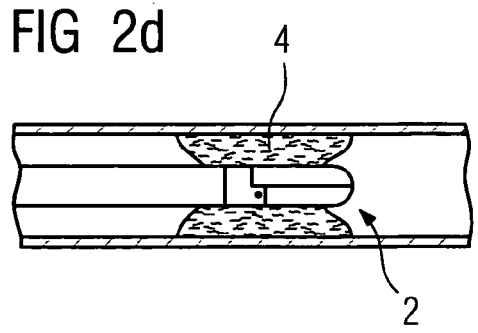

FIG. 1 shows a CTO catheter with a flexible catheter sheath 1, at the tip of which are disposed stretching tongs 2, which can be activated with the help of the likewise tong-type handle 3, so that it can be stretched outward from the folded position of the tong elements 2a and 2b shown in FIGS. 2a and 2d, as can be seen in FIGS. 2b and 2c, which show different stages of the opening of the plaque 4.

FIG. 3 shows a diagrammatic basic illustration of the structure of the CTO catheter with integrated IVUS monitoring to be used for removing stenoses according to the invention. Activation lines 5 and 6 are provided within the flexible catheter sheath 1 which lead from the activation handle 3 to the stretching tongs, whereby one line effects the opening movement of the tong elements and the other line effects their closing movement. This can be done using flexible rods or also more simply using taut wires. Also disposed in the flexible catheter sheath 1, alongside the activation lines 5 and 6, is a hollow flexible drive shaft 7 with signal lines 8 disposed therein for an IVUS sensor 9, which is disposed directly behind the stretching tongs within a ring-shaped window 10 of the catheter sheath 1 which is transparent for ultrasound waves. 11 represents a connection for contrast medium and irrigation fluid which can be pumped through the catheter sheath 1 to an outlet opening—not shown—disposed in the vicinity of the ring-shaped window 10. The combined catheter is connected to the signal interface and the drive unit for the IVUS system via the mechanical connection system 12, this being indicated in simplified form by the box 13. This mechanical connection system 12 contains a rotational coupling 14 for the connections.

FIG. 4 shows an exemplary embodiment in which instead of a rotating IVUS sensor a sensor array is used, formed by a plurality of ultrasound transducers 16 distributed equidistantly around the circumference of the catheter sheath 1. This embodiment has the advantage that no rotating parts are involved and therefore there is likewise no need for the flexible drive shaft 7 or the rotatable arrangement or the corresponding rotatable connection of the IVUS signal lines 8.

The invention is not limited to the exemplary embodiments shown. Thus magnetic navigation would also be possible, with permanent magnets or—alternatively—with electromagnets on the catheter tip or on the catheter, whereby these magnets and their position are not shown in the diagrams. In addition, an inflatable balloon—preferably even with several chambers—could be used in the vicinity of the tip, in order to bring the catheter tip to the required position and keep it there during the intervention, and—if possible—also to be used additionally as a dilatation balloon. This balloon is likewise not shown in the drawings. Furthermore, x-ray markers that are known per se could be provided on the catheter shaft, and also—of course—openings for a guidewire. Finally, it may be noted that the proposed solution of a combined CTO-IVUS catheter for the removal of complete stenoses is not limited to use in coronary arteries, but is essentially suitable for all types of vessels in the body.

Finally it would also be possible, unlike in the exemplary embodiments shown, to dispose the IVUS sensor forward of the stretching tongs. Besides the ability to push the rotating IVUS sensor through, as in the exemplary embodiment according to FIG. 3, an arrangement could also be provided in which the IVUS sensor can likewise be pushed through in a forward direction, but is designed as a sensor array as in FIG. 4, so that a rotational movement is not required.

The invention claimed is:

1. A medical device for removing a total vascular occlusion, comprising:
   a chronic total occlusion (CTO) catheter;
   stretching tongs arranged at a tip of the CTO catheter for removing the total vascular occlusion;
   an intravascular ultrasound (IVUS) catheter for monitoring a location within a vessel where the vascular occlusion is applied, wherein the CTO catheter and the IVUS catheter form one integrated catheter unit;
   a tube-shaped catheter outer jacket for accommodating the CTO catheter;
   a tube-shape catheter inner jacket disposed within the tube-shaped catheter outer jacket;
   a rotational coupler arranged to provide a rotational freedom of movement between the inner jacket and the outer jacket;
   a first activating line and a second activating line each respectively connected to the stretching tongs, wherein the first and second activating lines are arranged within the catheter outer jacket for opening and closing the stretching tongs;
   an IVUS sensor selectively positioned based on a mode of operation of the medical device, wherein the stretching tongs have an opening for passing the IVUS sensor through the opening, wherein in a first mode of operation the IVUS sensor is positioned upstream of the stretching tongs relative to the tip to observe an occlusion, wherein in a second mode of operation to permit deployment of the stretching tongues, the IVUS sensor is withdrawn through the opening to be positioned in correspondence with a circumferential ring-shaped window of the catheter outer jacket, wherein the ring-shaped window is transparent to ultrasound; and
   rotating IVUS signaling lines connected to the IVUS sensor, the rotating IVUS signaling lines arranged within the catheter inner jacket.

2. The medical device according to claim 1, wherein the rotating IVUS signaling lines are arranged within a hollow flexible drive shaft for driving the IVUS sensor, wherein the catheter inner jacket constitutes said drive shaft.

3. The medical device according to claim 1, wherein the rotating IVUS signaling lines are arranged within a hollow flexible drive shaft for driving the IVUS sensor, and the hollow flexible drive shaft is moveably supported within the catheter jacket such that the flexible drive shaft can be moved through the opening.

4. The medical device according to claim 1, wherein the catheter outer jacket comprises inlet and outlet openings for feeding to respectively discharging from the CTO catheter a contrast medium or a rinsing fluid.

5. The medical device according to claim 1, further comprising a plurality of magnets arranged at the tip for a magnetic navigation of the medical device within the vessel.

6. The medical device according to claim 1, further comprising an inflatable balloon arranged at the tip for fixing a position of the CTO catheter within the vessel or for vessel dilatation.

7. The medical device according to claim 6, wherein the balloon has a plurality of inflatable chambers.

8. The device according to claim 1, further comprising a continuous guide wire or a continuous guiding catheter.

9. A medical device for removing a total vascular occlusion, comprising:
   a chronic total occlusion (CTO) catheter;
   stretching tongs arranged at a tip of the CTO catheter for removing the total vascular occlusion;
   an intravascular ultrasound (IVUS) catheter for monitoring a location within a vessel where the vascular occlusion is applied, wherein the CTO catheter and the IVUS catheter form one integrated catheter unit;
   a tube-shaped catheter outer jacket for accommodating the CTO catheter;
   a tube-shape catheter inner jacket disposed within the tube-shaped catheter outer jacket, wherein the inner jacket and the outer jacket are arranged without a rotational freedom of movement relative to one another;
   an IVUS sensor array comprising a plurality of ultrasound transducers distributed around the catheter jacket, the IVUS sensor array selectively positioned based on a mode of operation of the medical device, wherein in a first mode of operation the IVUS sensor array is positioned upstream of the stretching tongs relative to the tip to observe an occlusion, wherein in a second mode of operation to permit deployment of the stretching tongues the IVUS sensor array is positioned downstream of the stretching tongs relative to the tip; and
   a first activating line and a second activating line each respectively connected to the stretching tongs, wherein the first and second activating lines are arranged within the catheter outer jacket for opening and closing the stretching tongs without a slidable movement of the inner and outer jackets with respect to one another; and
   IVUS signaling lines connected to the IVUS sensor array.

* * * * *